United States Patent
Krummenacher et al.

(10) Patent No.: US 10,668,200 B2
(45) Date of Patent: Jun. 2, 2020

(54) HANDLE FOR A MEDICAL DEVICE

(71) Applicant: Debiotech S.A., Lausanne (CH)

(72) Inventors: Renaud Krummenacher, Lausanne (CH); Frédéric Neftel, Crans-Montana (CH)

(73) Assignee: Debiotech S.A., Lausanne (CH)

( * ) Notice: Subject to any disclaimer, the term of this patent is extended or adjusted under 35 U.S.C. 154(b) by 357 days.

(21) Appl. No.: 15/508,914

(22) PCT Filed: Oct. 15, 2015

(86) PCT No.: PCT/IB2015/057923
§ 371 (c)(1),
(2) Date: Mar. 4, 2017

(87) PCT Pub. No.: WO2016/059589
PCT Pub. Date: Apr. 21, 2016

(65) Prior Publication Data
US 2017/0246369 A1     Aug. 31, 2017

(30) Foreign Application Priority Data

Oct. 17, 2014   (EP) .................................... 14189391

(51) Int. Cl.
*A61M 1/16*     (2006.01)
*A61M 5/14*     (2006.01)
(Continued)

(52) U.S. Cl.
CPC ........... *A61M 1/1652* (2014.02); *A61B 50/20* (2016.02); *A61M 1/28* (2013.01); *A61M 5/1415* (2013.01); *A61M 2209/082* (2013.01)

(58) Field of Classification Search
CPC .... A61M 1/1652; A61M 1/28; A61M 5/1415; A61M 2209/082; A61M 1/14;
(Continued)

(56) References Cited

U.S. PATENT DOCUMENTS

| | | | |
|---|---|---|---|
| 3,603,550 A * | 9/1971 | Byrd ...................... | A62C 13/78 211/85.18 |
| 4,211,380 A | 7/1980 | Lillegard et al. | |

(Continued)

FOREIGN PATENT DOCUMENTS

| WO | WO0108722 A2 | 2/2001 |
|---|---|---|
| WO | WO2015/177606 | 11/2015 |

OTHER PUBLICATIONS

International Search Report for PCT/IB2015/057923, dated Jan. 26, 2016.
(Continued)

*Primary Examiner* — David C Mellon
(74) *Attorney, Agent, or Firm* — Andre Roland S.A.; Nikolaus Schibli

(57) ABSTRACT

A handle assembly for a medical device including an element for grasping having an opening, the opening configured to allow for passage of fingers of a user, a mechanical-connection element configured to fix the element for grasping to the medical device, and a support configured to receive and at least temporarily fix an additional device on the element for grasping, the support attached to the element for grasping, wherein when the additional device is received by the support, the element for grasping together with the additional device form a handle of the handle assembly configured to be grasped by hand of the user.

10 Claims, 4 Drawing Sheets

(51) Int. Cl.
*A61B 50/20* (2016.01)
*A61M 1/28* (2006.01)

(58) Field of Classification Search
CPC .... A61M 1/16; A61M 1/1621; A61M 1/1623; A61M 1/3633; A61M 1/3635; A61M 2205/12; A61M 2205/121; A61M 2205/125; A61M 2205/126; A61M 2209/08; A61M 2209/084; A61M 2209/086; A61B 50/20
See application file for complete search history.

(56) References Cited

U.S. PATENT DOCUMENTS

| | | | | | |
|---|---|---|---|---|---|
| 5,770,064 | A | * | 6/1998 | Jonsson | A61M 1/3644 210/232 |
| 5,772,624 | A | * | 6/1998 | Utterberg | A61M 1/3621 128/898 |
| 5,895,571 | A | * | 4/1999 | Utterberg | A61M 1/3606 210/241 |
| 6,250,482 | B1 | * | 6/2001 | Want | A61G 7/0503 211/133.4 |
| 10,195,334 | B2 | * | 2/2019 | Appling | A61M 1/3679 |
| 2004/0064080 | A1 | * | 4/2004 | Cruz | A61M 1/16 604/5.04 |
| 2007/0252057 | A1 | * | 11/2007 | Utterberg | A61M 1/16 248/218.4 |
| 2010/0270225 | A1 | * | 10/2010 | Haecker | A61M 1/16 210/232 |
| 2013/0299661 | A1 | * | 11/2013 | Schade | B01D 65/00 248/313 |
| 2015/0306305 | A1 | * | 10/2015 | Kluttz | A61M 5/1418 248/219.4 |

OTHER PUBLICATIONS

Written Opinion of the International Searching Authority, for PCT/IB2015/057923, dated Jan. 26, 2016.

\* cited by examiner

HANDLE FOR A MEDICAL DEVICE

CROSS REFERENCE TO RELATED APPLICATIONS

The present application is a U.S. national stage application of PCT/IB2015/057923 filed on Oct. 15, 2015 designating the United States, and claims foreign priority to the European Patent Application No. EP 14189391.7 filed on Oct. 17, 2014, the contents of both documents being herewith incorporated by reference in their entirety.

FIELD OF THE INVENTION

The invention relates to a handle of a medical device which allows the medical device to be grasped but which is also used as a support for a distinct element of the medical device, for example a filter.

PRIOR ART

Certain medical devices are provided with a handle. This handle is nothing more than an element that allows the medical device to be transported or manipulated, in other words it has no function other than the conventional function of a handle. Now, this practical element has a certain cost for a function which, although practical, is not a very fundamental one.

On the other hand, certain systems such as dialysis systems comprise functional elements for treatment, but these functional elements may be elements distinct from the "main" apparatus. This is the case for example with the filter of a hemodialysis system which during treatment is held on the apparatus in a certain position (preferably vertically, so as to allow bubbles to escape). Thus, during treatment, these elements are held together. These medical systems are therefore provided with a support which has no other function than to hold said element against the "main" apparatus. Documents bearing the following publication numbers: U.S. Pat. No. 4,211,381 A, U.S. 2010/270225 A1 and WO 01/08722 A2 set out filter support systems but the support is not a handle for a device. In other words, each element has just the one single function, and this is not economically optimal.

GENERAL DESCRIPTION OF THE INVENTION

The chief objective of the present invention is to alleviate the disadvantages of the known systems by proposing to combine the handle and element-support functions. Synergy is thus created so as to minimize the number of component parts with a view to cost savings and/or optimization of functions, bulk and/or to rationalizing the use of the device.

A medical system may comprise at least one disposable device and/or at least one reusable device. In general, a disposable device is a single-use device so that after it has been used the disposable device cannot be reused. The disposable device is disposed of because it comprises at least one element (fluidic path for example) which has come into contact with a fluid which may be the blood of the patient, a drug solution or the like. Reusing such a device would require steps of cleaning and expensive sterilizing which could adversely affect the device. In addition, said element may be difficult to detach or inseparable from the device and this is why the entire device comprising this element is then considered to be a single-use device. For example, a disposable device may be a filter through which a fluid (for example dialysate and/or blood) passes. In contrast, a reusable device is a device that can be used several times. Thus, a reusable device can be used in succession with several disposable devices and, conversely, a disposable device can be used with only one reusable device.

In particular, in the field of hemodialysis, the medical system comprises at least one reusable device (also referred to as the permanent device) which generally comprises the more sophisticated or expensive elements (for example: the electronics, the sensors, the actuators, etc.) and at least one disposable device. This may notably be a fluidic distribution part (cassette, tube, bag, heating pouch, etc.), the filter and, in some instances, a sorbent device which allows the used dialysate to be filtered so that it can be recycled, for example by absorption or adsorption of certain substances contained in the filtered solution. In some cases, some of these elements may be reused, for example after cleaning.

During the use of such medical systems, certain elements of the disposable device may be held by another device such as the permanent device. For example, the filter (disposable device) may be held by the main apparatus (permanent device) during the treatment. By way of information, a filter is a disposable device through which there circulates, on the one hand, the patient's blood circulates and, on the other hand, a fluid (dialysate) circulates with a view to performing the necessary exchanges (urea, water, etc.) between these two fluids as a kidney would do.

In the context of the invention, the support (used for example to fix the filter) is an element of the carry handle of the device. In other words, the handle comprises a support allowing the removable attachment of another element such as a filter. This other element may be a disposable or reusable device. For ease of reading, the word filter will be used to denote this other element and the term main device will be used to denote the device to which the support is fixed (the main device may or may not be the main apparatus). The main device may be a cycler and/or comprise (removably or otherwise) a sorbent.

Thus, said handle has a dual function; that of handling, holding or carrying the device (to which it is fixed) and that of holding the filter. The benefit is a major one and the filter and its support thus form an element that a user can easily grasp. This assembly forms the handle of the device. The main device or the filter can thus be transported and/or manipulated simply by grasping a single element (the handle) while maintaining the functional position (angle) of the filter.

The support/filter assembly is designed to be easily grasped by the hand of a user. However, it is possible for the support without the filter to be designed likewise to be grasped by the hand of a user, and so the handle may be functional even without the filter.

In one embodiment, the main device is a disposable device. In other words, the filter is held on a disposable device. Thus, at the end of treatment, the assembly comprising filter and main device (which is disposable) is disposed of without the need to separate them. That allows the manipulation of the assembly to be made easier. The disposable device may be the sorbent or a fluidic distribution system.

In another embodiment, the main device is a reusable device. In other words, the filter is held on a permanent device, while allowing grasping through said handle of the permanent device.

One of the problems relating to a handle is that it may be used to carry around a device (permanent or disposable) of a certain weight (500 g or more). A filter (of somewhat tubular and/or longitudinal shape) in itself represents an ideal handle on account of its shape. However, if the filter is the only element for grasping that forms the handle of the main device then it is necessary for the filter to be robust enough to perform its handle function. Thus, in one embodiment, the handle comprises an element for grasping mechanically coupled to the support in such a way as to limit the mechanical stresses applied to the filter when it is being used as a handle. In that case, the support is designed to accept and firmly hold the filter on the element for grasping.

Thus, one of the novel features of the invention is that it uses the handle as a support for the filter (with the possibility of fixing, for example by clipping), while at the same time also allowing the filter to be grasped in the hand through the handle itself. Thus it is the support element of the handle rather than the filter that is subjected to the main mechanical forces (while at the same time making use of the cylindrical shape of the filter to constitute the definitive easy-to-grasp shape of the handle).

LIST OF FIGURES

The invention will be better understood hereinafter by means of a number of illustrated examples.

It goes without saying that the invention is not restricted to these embodiments.

FIG. 1 schematically depicts one example of a hemodialysis system comprising a sorbent unit.

Figure 6:
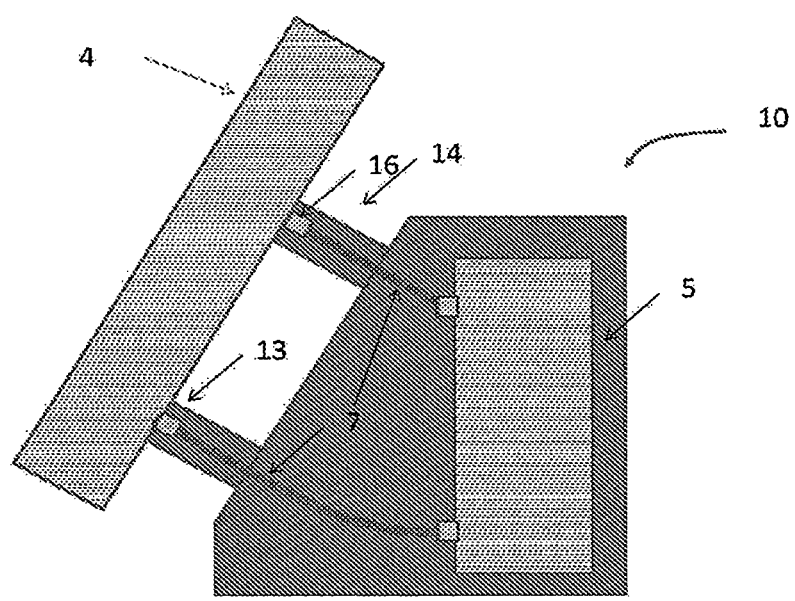

FIG. 6 schematically depicts an embodiment in which all or part of a fluidic path is comprised within the main device.

Figure 7:
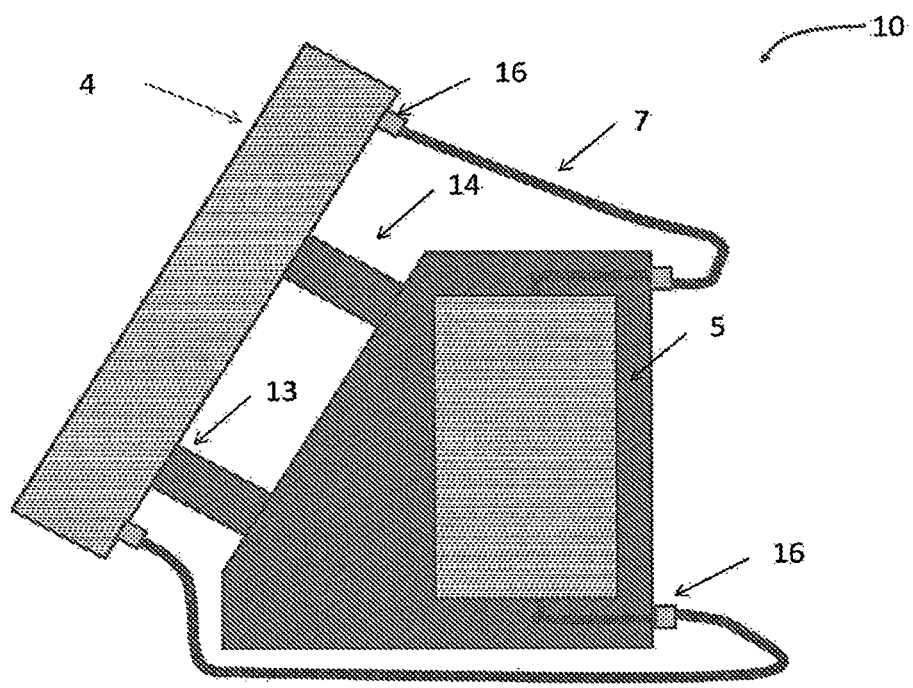

FIG. 7 schematically depicts an embodiment in which most of the fluidic path of the dialysate is external to the main device.

Figure 8:
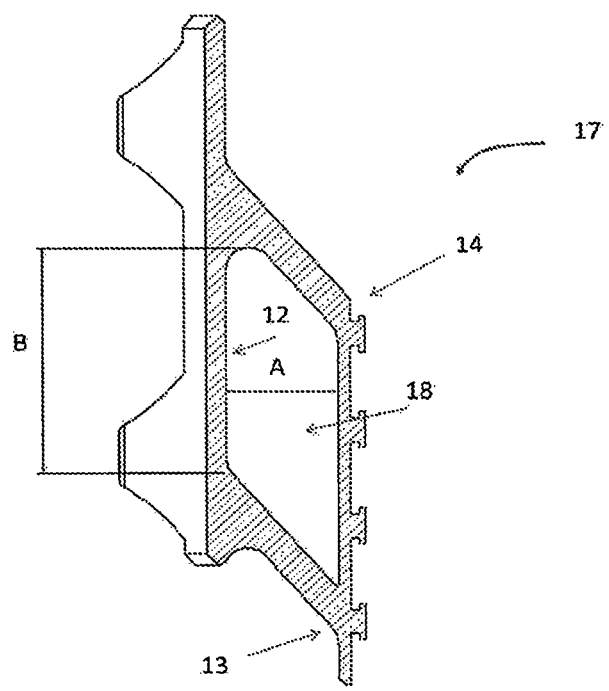

FIG. 8 is a view in cross section of the handle/support assembly.

NUMERICAL REFERENCES USED IN THE FIGURES

1 Hemodialysis system
2 Patient
3 Main apparatus
4 Filter
5 Sorbent
6 Blood circuit
7 Dialysate circuit
10 Main device (i.e. comprising a handle as described by the invention)
11 Filter support
12 Element for grasping
13, 14 Mechanical-connection elements
15 Hand of a user
16 Fluidic connection port/connector
17 Handle/support assembly
18 Passage orifice

DETAILED DESCRIPTION OF THE INVENTION

In the present document, the detailed description of the invention comprises embodiments of devices, systems and methods which have been set out by way of illustration. Of course other embodiments are conceivable and may be applied without departing from the scope or spirit of the invention. The following detailed description must not, therefore, be considered to be limiting.

Unless indicated otherwise, the scientific and technical terms used in the present document have meanings commonly used by those skilled in the art. The definitions given in this document are mentioned with a view to assisting with the understanding of the terms frequently used and are not intended to limit the scope of the invention.

The directional indications used in the description and the claims, such as "top", "bottom", "left", "right", "upper", "lower" and other directions or orientations are mentioned with a view to providing greater clarity with reference to the figures. These indications are not intended to limit the scope of the invention.

The verbs "to have", "to compromise", "to include" or equivalent are used in the present document in a broad sense to mean in general "include but not limited thereto".

The term "or" is generally used in a broad sense encompassing "and/or" unless the context clearly indicates the contrary.

In this document, the term "handle" is to be understood as meaning an element or an assembly of elements which is fixed to a device and which has at least the substantial function of handling, holding or carrying said device and which is designed to be grasped in at least one hand of a user.

Figure 1:
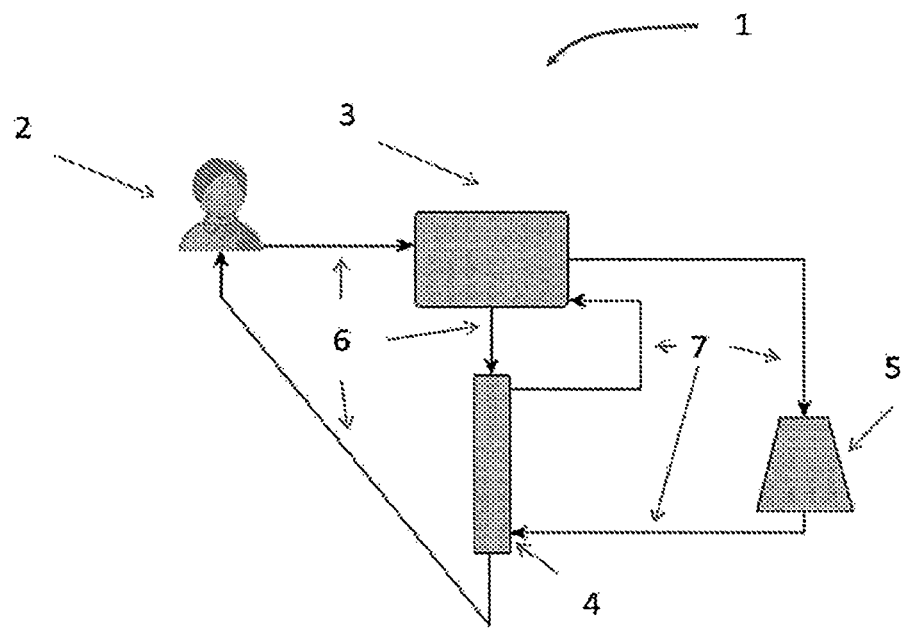

FIG. 1 gives a brief schematic depiction of one example of a hemodialysis system (1). The system comprises two distinct circuits (6, 7), the first for blood and the second for dialysate. The blood is taken from the patient by a blood pump arranged in the main apparatus (the cycler) (3). The blood will then pass into the filter (4) to be purified and will then return to the patient (2). The circuit for the dialysate (7) may differ depending on the system. It may comprise a bag of fresh dialysate which will enter the filter (4). This used dialysate may then be stored in a dedicated bag. In our example, a device of the sorbent type (5) is arranged between the main apparatus (3) and the filter (4). In other systems, the sorbent may be arranged elsewhere. Thus, thanks to the sorbent, the used dialysate can be rinsed of its impurities so that it can be reused during the treatment (possibly with its liquid content reconstituted with a liquid containing concentrated solutes needed to reconstitute the dialysate from, for example, water). FIG. 1 may also schematically depict one example of a peritoneal dialysis system with reconstitution of the dialysate. In that case, the fluidic path (6) contains dialysate which is injected into and then removed from the peritoneal cavity of the patient. The fluidic path (7) would then in this case allow the used dialysate removed from the patient to be "washed" so that it can be reused.

Normally, anything that has been wetted by the blood or by the dialysate is single-use. In order to avoid having to dispose of the main apparatus (the cycler) (3), the system for example uses a cassette (not depicted) which acts as an interface between the main apparatus and the fluid. In this way, only the cassette is disposed of. The cassette, the filter (4) and the sorbent (5) are in fluidic communication through the circuit for the dialysate (7) and are therefore in general also intended to be single-use.

The filter takes the form of an element comprising a longitudinal main body and two opposite ends. At or near these ends, tubes allow fluidic connection with the blood circuit and dialysate circuit.

Figure 2:
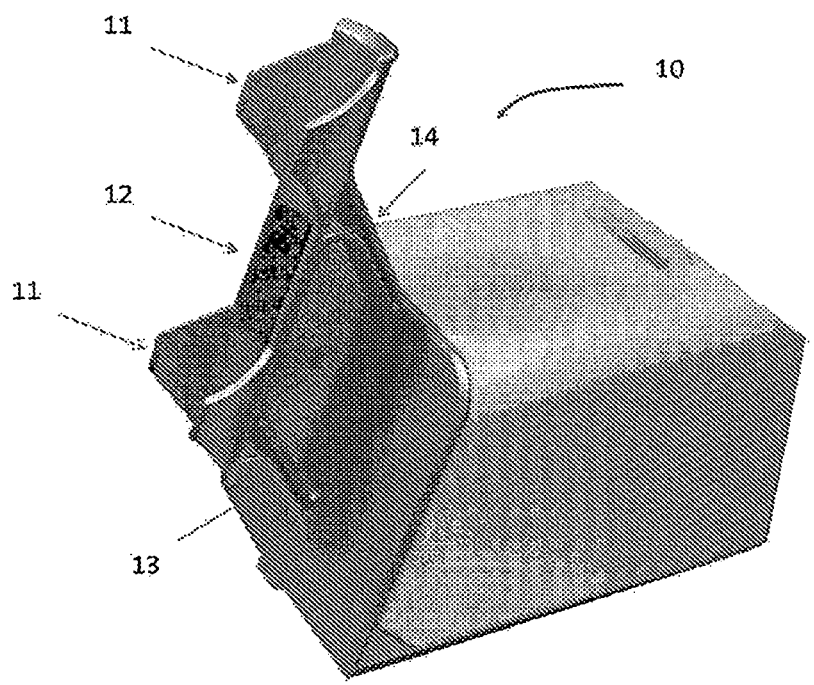
FIG. 2 shows the device comprising a handle as described by the present invention.

FIG. 2 illustrates a preferred embodiment; the main device (10) comprises a handle firmly fixed and/or fixedly connected to the device via at least one mechanical-connection means (13, 14). The handle may comprise an element for grasping (12) which may allow the hand of the user to pass between the handle and the device (10). By virtue of this element for grasping, the handle can be used without the filter but also allows the mechanical strength of the assembly to be improved appreciably. The handle further comprises at least one support designed to hold the filter removably on the element for grasping. In one embodiment, a sorbent is placed inside the main device or the sorbent is the main device. In the latter instance, the sorbent will have legs so that it can be stood on a surface while being used (during treatment).

In an embodiment divulged in FIG. 6, all or part of the fluidic path (7) connecting the filter (4) to the sorbent (5) may be arranged inside the main device and/or in the mechanical-connection elements (13, 14). The main device may also comprise fluidic connectors designed to fluidically connect the filter and/or the sorbent to the fluidic path (6, 7). The fluidic paths may be tubes fixed removably or nonremovably to the main device and/or to the mechanical-connection elements (13, 14).

In an embodiment divulged in FIG. 7, the sorbent (5) and the filter (4) are fluidically connected via connecting tubes and connecting ports (16). A fluid distribution system, like the one described in international patent application PCT/IB2014/063214 (the entire content of that document is incorporated by reference into the present application) can be used for transporting the fluid through the fluidic path (7). These tubes and ports may be arranged on the outside of the device.

Figure 3:
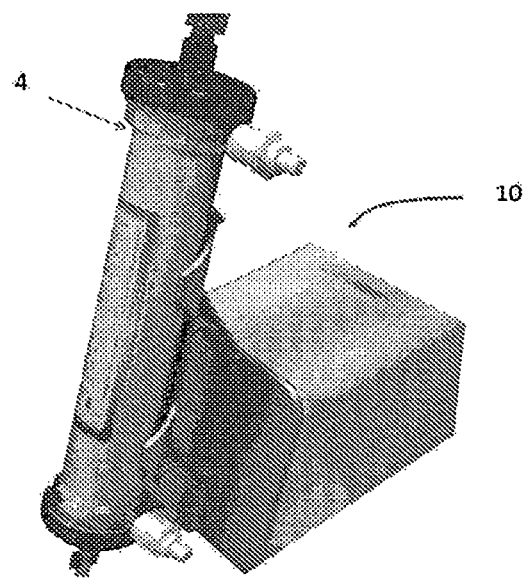
FIG. 3 illustrates the arranging of the filter on the handle.

FIG. 3 sets out the arrangement of the filter (4) on the device (10). In that embodiment, the element for grasping (12) extends longitudinally against the body of the filter (4). The support may comprise one or two elements arranged substantially at the two ends of the element for grasping and/or near the ends of the filter.

Figure 4:
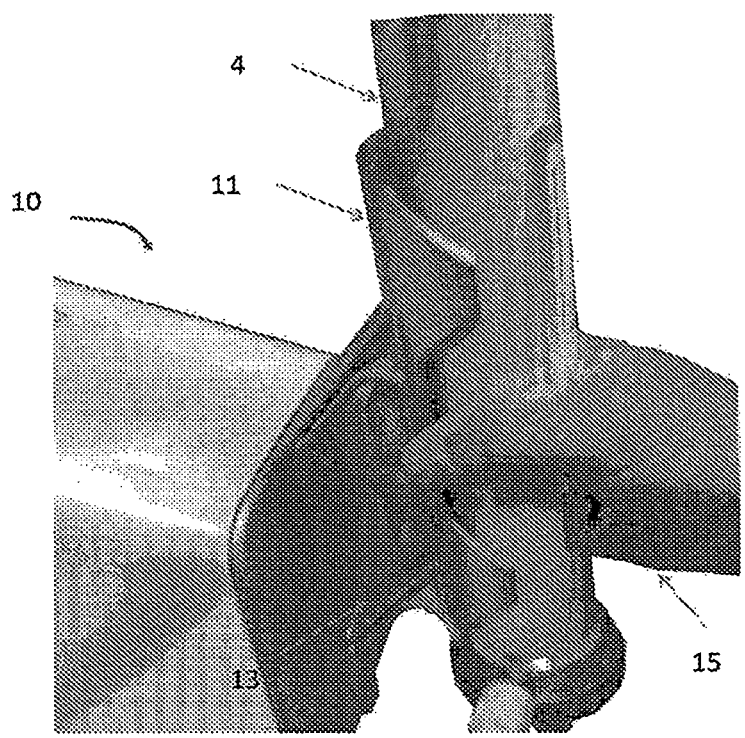
FIG. 4 illustrates the grasping of the assembly by the hand of the user.

FIG. 4 illustrates the grasping of the handle by the hand of a user (15). Thus, the filter (4) and the element for grasping (12) form an assembly designed to be easily grasped by the hand of a user while the element for grasping and the filter are completely distinct elements. The existence of this element for grasping (12) makes it possible to avoid transferring most of the mechanical stress to the body of the filter (4) and therefore does not require the fixing of the filter to the handle to be necessarily secure. In other words, even when the device is heavy, the element for grasping provides sufficient mechanical strength that the filter does not experience excessive amounts of stress that could damage it or that the assembly does not require secure fixing between the filter and the handle itself.

Figure 5:
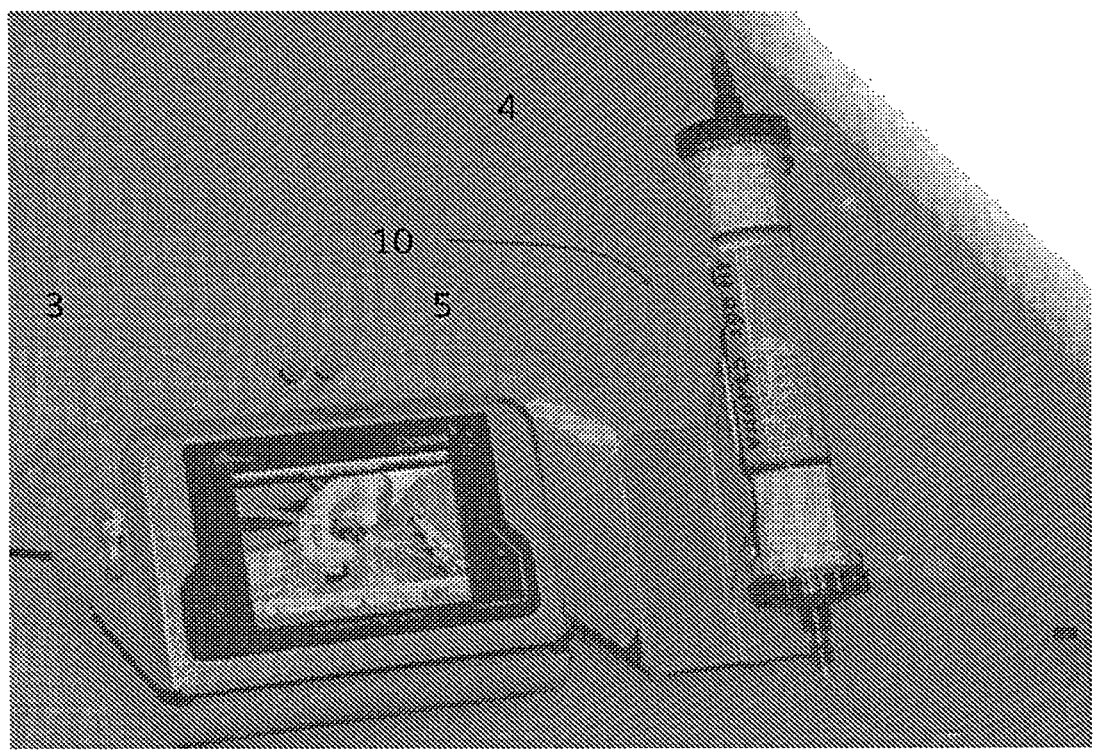
FIG. 5 depicts a complete hemodialysis system.

In an embodiment divulged in FIG. 5, the complete medical system comprises a main apparatus (3), a filter (4) held on a main device (10) comprising the handle. In this embodiment, the device is a sorbent device (5). In this embodiment the main apparatus and the main device are distinct but in another embodiment, the main device may be the main apparatus.

In one possible embodiment, the element for grasping (with or without the filter), the support and/or the mechanical-connection elements may be detached from the main device so that they can be reused with another main device.

In another embodiment, an assembly made up of at least two distinct elements forms a handle of a medial device. This medical device may be a disposable or reusable device of a medical system. Said assembly comprises a first element and a second element which is distinct from the medical device and from the first element. This assembly is designed to be grasped by the user by means of a hand. The second element may be provided with a shape ensuring ease of grasping, for example a cylindrical and/or longitudinal shape. The second element may also be held reversibly on the first element, the latter thus forming a support element for the second. The assembly thus forms an element for lifting the medical device designed to be grasped in one hand in order to lift/transport/move the medical device. The second element may further be a functional element of the medical system. For example, it may be designed to perform a task/action needed in the therapy of a patient.

The Assembly Being

FIG. 8 sets out the handle/support assembly without the main device (10) and without the filter (4). This assembly may be attached removably to the main device by virtue of the mechanical-fixing elements (13, 14) which may comprise coupling elements (for example in the form of a button) which fit together with coupling elements suited to the main device.

FIG. 8 also sets out the passage orifice (18) through which the user at least partially introduces his hand in order to grasp the handle, for example the element for grasping (12) (with or without the filter). The distance A may be comprised between 1 and 10 cm, ideally between 2 and 5 cm, for example substantially equal to 3 cm. The distance B may be comprised between 4 and 30 cm, ideally between 5 and 15 cm, for example substantially equal to 8 cm.

According to one embodiment, the handle comprises an element for grasping which is situated at a distance from the medical device that allows the passage of the fingers, a mechanical-connection element allowing the element for grasping to be fixed (for example mechanically) to the medical device and a support suited to receiving and fixing (for example mechanically) an additional device on the element for grasping. Thus, the additional device and the element for grasping are distinct elements which form a handle assembly designed to be grasped by the hand of a user. Furthermore, the additional device has a substantially therapeutic function. The additional may be a functional element for purifying the patient's blood, for example a filter.

For preference, the additional device may be fixed removably to the support.

In addition, the element for grasping may extend longitudinally along the additional device. The support may comprise at least one additional-device-fixing element arranged on the element for grasping or two additional-device-fixing elements arranged for example substantially at the two ends of the element for grasping.

The element for grasping may be fixed removably to the medical device. Furthermore, the element for grasping, with or without the additional device, may be detached from the assembly of the medical device in order to be placed on a new medical device.

The invention also describes a medical device that may comprise a handle similar to the one divulged in the document. According to one embodiment, the medical device is disposable as is the additional device, after a single use, so that the assembly comprising medical device and additional device can be disposed of easily.

In addition, the medical device may be fluidically connected to the additional device and may comprise a sorbent for dialysis fluid. Thus, the medical device is an element of a peritoneal dialysis system or an element of a hemodialysis system.

Stated differently, the handle of the invention may comprise two distinct parts: a first part which comprises an additional device designed to be grasped by a hand of a user and a second part which comprises mechanical-connection elements allowing a support intended to receive and removably fix said first part to be fixed to the medical device. For preference, the mechanical-connection elements are arranged in such a way as to create a passage orifice through which a user can introduce a hand at least partially. Furthermore, the additional device may have a substantially therapeutic function.

The invention claimed is:

1. A handle assembly for a medical device comprising:
   an element for grasping having an opening, the opening configured to allow a passage of fingers of a user,
   a mechanical-connection element configured to fix the element for grasping to the medical device, and
   a support configured to fix an additional device on the element for grasping,
   wherein when the additional device is received by the support, the element for grasping together with the additional device are configured as a handle of the handle assembly configured to be grasped by hand of the user,
   wherein the additional device is configured to perform a filtering function, and
   wherein the additional device is removably fixed to the support.

2. The handle assembly as claimed in claim 1, wherein the additional device includes a device for purifying blood of a patient.

3. The handle assembly as claimed in claim 1, wherein the additional device includes a blood filter.

4. The handle assembly as claimed in claim 1, wherein the element for grasping extends longitudinally along the additional device.

5. The handle assembly as claimed in claim 1, wherein the support includes an additional-device-fixing element arranged on the element for grasping.

6. The handle assembly as claimed in claim 1, wherein the support includes two additional-device-fixing elements arranged substantially at two ends, respectively, of the element for grasping.

7. The handle assembly as claimed in claim 1, wherein the element for grasping is removably fixed to the medical device.

8. A peritoneal dialysis system including a medical device, the medical device including a handle assembly, the handle assembly comprising:
   an element for grasping having an opening, the opening configured to allow for passage of fingers of a user,
   a mechanical-connection element configured to fix the element for grasping to the medical device, and
   a support configured to receive and at least temporarily fix an additional device on the element for grasping, the support attached to the element for grasping,
   wherein when the additional device is received by the support, the element for grasping together with the additional device form a handle of the handle assembly configured to be grasped by hand of the user,
   wherein the additional device is configured to perform a medical function, and
   wherein the medical device and the additional device are disposable following a single use, so that the handle assembly can be disposed of.

9. A hemodialysis system including a medical device, the medical device including a handle assembly, the handle assembly comprising:
   an element for grasping having an opening, the opening configured to allow for passage of fingers of a user,
   a mechanical-connection element configured to fix the element for grasping to the medical device, and
   a support configured to receive and at least temporarily fix an additional device on the element for grasping, the support attached to the element for grasping,
   wherein when the additional device is received by the support, the element for grasping together with the additional device form a handle of the handle assembly configured to be grasped by hand of the user,
   wherein the additional device is configured to perform a medical function, and
   wherein the medical device and the additional device are disposable following a single use, so that the handle assembly can be disposed of.

10. A handle assembly for a medical device comprising:
    an element for grasping having an opening, the opening configured to allow a passage of fingers of a user,
    a mechanical-connection element configured to fix the element for grasping to the medical device, and
    a support configured to fix an additional device on the element for grasping,
    wherein when the additional device is received by the support, the element for grasping together with the additional device are configured as a handle of the handle assembly configured to be grasped by hand of the user,
    wherein the additional device is configured to perform a filtering function, and
    wherein the additional device is non-removably fixed to the support.

* * * * *